United States Patent [19]
Errico et al.

[11] Patent Number: 5,578,033
[45] Date of Patent: *Nov. 26, 1996

[54] ADVANCED POLYAXIAL LOCKING HOOK AND COUPLING ELEMENT DEVICE FOR USE WITH SIDE LOADING ROD FIXATION DEVICES

[75] Inventors: Joseph P. Errico, Far Hills; Thomas J. Errico, Summit; James D. Ralph, Oakland, all of N.J.

[73] Assignee: Fastenetix, L.L.C., Summit, N.J.

[*] Notice: The term of this patent shall not extend beyond the expiration date of Pat. No. 5,549,608.

[21] Appl. No.: 542,542

[22] Filed: Oct. 13, 1995

Related U.S. Application Data

[63] Continuation-in-part of Ser. No. 502,285, Jul. 13, 1995.

[51] Int. Cl.⁶ .................................................. A61B 17/70
[52] U.S. Cl. ............................................ 606/61; 606/72
[58] Field of Search ........................... 606/61, 69, 70, 606/71, 72, 73, 66, 65, 59, 54, 104

[56] References Cited

U.S. PATENT DOCUMENTS

| | | |
|---|---|---|
| 4,805,602 | 2/1989 | Puno et al. . |
| 4,946,458 | 8/1990 | Harms et al. .............................. 606/61 |
| 4,987,892 | 1/1991 | Krag et al. ................................. 606/61 |
| 5,151,103 | 9/1992 | Tepic et al. ................................ 606/69 |
| 5,176,680 | 1/1993 | Vignaud et al. ........................... 606/61 |
| 5,181,917 | 1/1993 | Rogozinski ................................ 606/61 |
| 5,190,543 | 3/1993 | Schläpfer ................................... 606/61 |
| 5,207,678 | 5/1993 | Harms et al. .............................. 606/61 |
| 5,217,497 | 6/1993 | Mehdian ..................................... 623/17 |
| 5,261,909 | 11/1993 | Sutterlin et al. ........................... 606/61 |
| 5,261,912 | 11/1993 | Frigg ......................................... 606/61 |
| 5,306,275 | 4/1994 | Bryan ........................................ 606/61 |
| 5,346,493 | 9/1994 | Stahurski et al. ......................... 606/61 |
| 5,360,431 | 11/1994 | Puno et al. ................................. 606/72 |
| 5,374,267 | 12/1994 | Siegal ........................................ 606/61 |
| 5,443,467 | 8/1995 | Biedermann et al. ..................... 606/65 |
| 5,480,401 | 1/1996 | Navas ........................................ 606/61 |

*Primary Examiner*—Guy V. Tucker
*Attorney, Agent, or Firm*—Joseph P. Errico

[57] ABSTRACT

A hook device for use with support rod implantation apparatus in the spine, having a rod receiving body polyaxially mounted to a blade portion such that the body may be polyaxially maneuvered relative to the placement of the blade, for easy rod coupling. The blade portion of the device has a semi-spherical head portion which sits above the lamina. The rod receiving portion is a separate coupling element having lower, intermediate, and upper portions. The lower portion is slotted and tapered, and has a semi-spherical interior chamber in which the semi-spherical head is polyaxially disposed. The intermediate portion has a side recess for receiving the rod. The top portion is threaded for a top locking nut. A locking ring is disposed about the coupling element, the top of the coupling element being initially positioned above the lower ledge of the side recess such that the rod initially seats against the top surface of the locking ring. A rod retaining sleeve is provided about the coupling element; the sleeve having a lower surface which seats against the top of the rod. When the rod is in place, the top locking nut is tightened to provides a downward force onto the sleeve. The sleeve, in turn, applies a force against the rod, which causes the locking ring to descend down the tapered lower portion, therein locking the semi-spherical head in the interior chamber of the coupling element, and locking it into position relative to the blade portion.

13 Claims, 6 Drawing Sheets

ADVANCED POLYAXIAL LOCKING HOOK AND COUPLING ELEMENT DEVICE FOR USE WITH SIDE LOADING ROD FIXATION DEVICES

CROSS-REFERENCE TO PRIOR APPLICATION

This invention is a continuation-in-part of co-pending application, U.S. Ser. No. 08/502,285, filed Jul. 13, 1995, still pending, entitled "An Advanced Polyaxial Locking Screw And Coupling Element Device For Use With Rod Fixation Apparatus".

BACKGROUND OF THE INVENTION

1. Field of the Invention

This invention relates generally to a polyaxial locking spinal fixation device. More particularly, the present invention relates to a hook and coupling element assembly for attaching to the posterior lamina portion of the spine and for polyaxially receiving and holding securely a rod of an implantation apparatus using same.

2. Discussion of the Prior Art

The bones and connective tissue of an adult human spinal column consist of an upper portion having more than 20 discrete bones, and a lower portion which consists of the sacral bone and the coccygeal bodies. The bones of the upper portion are generally similar in shape, as will be more fully described hereinbelow with respect to FIGS. 1 and 2. Despite their similar shape, however, they do vary substantially in size in accordance with their individual position along the column and are, therefore, anatomically categorized as being members of one of three classifications: cervical, thoracic, or lumbar. The cervical portion, which comprises the top of the spine, up to the base of the skull, includes the first 7 vertebrae. The intermediate 12 bones are the thoracic vertebrae, and connect to the 5 lumbar vertebrae.

Figure 1:
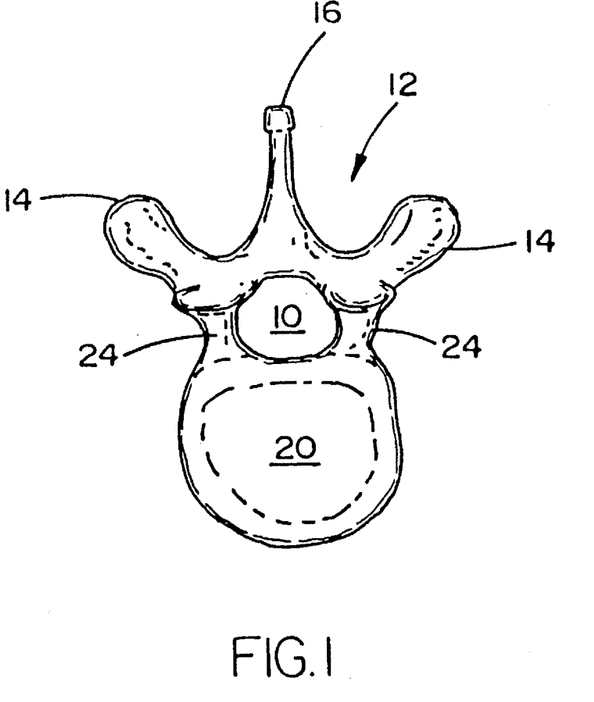
FIG. 1 is a top view of a vertebral bone characteristic of those of the cervical, thoracic, and lumbar spine.
Figure 2:
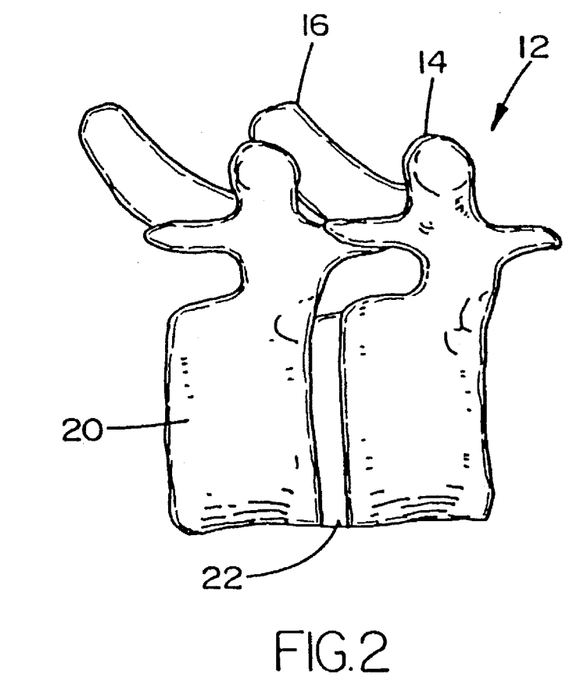
FIG. 2 is a side view of sequentially aligned vertebral bones, such as are found in the cervical, thoracic, or lumbar spine.

These bones of the upper portion vary in size, but are each similarly coupled to the next by a tri-joint complex. The tri-joint complex consists of an anterior disc and the two posterior facet joints; the anterior discs of adjacent bones being cushioned by cartilage spacers referred to as intervertebral discs. Referring now to FIGS. 1 and 2, top and side views of a typical vertebral body of the upper portion of the spinal column is shown. The spinal cord is housed in the central canal 10, protected from the posterior side by a shell of bone called the lamina 12. The lamina 12 has three large protrusions, two of these extend laterally from the side ends thereof and are referred to as the transverse process 14. The third extends back and down from the center of the lamina and is called the spinous process 16.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

The lower portion of the spinal column, which extends into the hip region is primarily comprised of the sacral bone. This bone is unlike the other bones of the spinal column, in both shape and size. In fact, at birth humans have five distinct sacral bones which begin to fuse together during childhood, and by adulthood have fully combined. For the purpose of describing this invention, however, the sacral bone shall be referred to as distinct from the spinal column; the spinal column, therefore, comprising for the purposes of this description, only the cervical, thoracic, and lumbar vertebrae.

In its entirety, the spinal column is highly complex in that it houses and protects critical elements of the nervous system which have innumerable peripheral nerves and arterial and veinous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally by coupling to the pedicles via screws, or by means of hooks which attach under the lamina and entering into the central canal. In either case, the implants generally comprise elongate support rod elements which are coupled to the screws or hooks to immobilize several sequential vertebrae, for example to hold them stable so that the adjacent bones may be fused with bone graft. The prior co-pending application, U.S. Ser. No. 08/502,285, of which this application is a continuation-in-part, discloses novel devices which provide significantly superior performance for such implants which comprise screws for coupling to the pedicles. The present invention relates to corresponding implant apparatus which utilize hooks.

Such hook and rod assemblies generally comprise a plurality of hooks having rounded blade portions which are inserted posteriorly under the lamina between the transverse process and the spinous process, and upper body portions to which the support rod is coupled. The rod extends along the axis of the spine, coupling to each of a plurality of hooks via receiving portions of their bodies. The aligning influence of the rod forces the spine to which it is affixed, to conform to a more proper shape.

It has been identified, however, that a considerable difficulty may be associated with inserting hooks under sequential lamina along a misaligned curvature and simultaneously exactly positioning their rod receiving portions such that they are aligned so that the rod can be passed therethrough without distorting, tilting, rotating, or exerting undesired translational forces on the hooks. Correction of this difficulty requires the time consuming and difficult task of reshaping the rods or repositioning the hooks, each of which is understood to require considerably longer operating time, which is known to increase the incidence of complications associated with surgery. Often such alignments with such fixed body hooks cannot be satisfactorily achieved, and the entire instrumentationing effort has to be altered to utilizing screws.

It is, therefore, the principal object of the present invention to provide a lamina hook having a rod coupling body which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a lamina hook having a polyaxial coupling body for use with rod stabilization and immobilization systems in the spine. More particularly, the hook comprises a curvate flat hook shaped blade portion having a ball shaped head. The body of the device comprises a separate coupling element mounted on the ball shaped (semi-spherical) head so that it is rotationally free prior to secure fixation of the rod thereto, and which is securely locked in a given angulation once the rod is received by the coupling element. The coupling element has a generally cylindrical main body portion, a locking ring, an external rod securing sleeve, and a top locking nut.

The coupling element may be conceptually divided into a lower socket portion, an intermediate rod receiving portion, and a top nut receiving portion. The lower socket portion is designed with an interior chamber having an opening at the bottom of the coupling element. The interior chamber is provided for receiving therein the head of the blade portion such that the blade and the coupling element are held together, but prior to the securing of the rod to the intermediate portion, the blade and coupling element remain free to swing and rotate freely with respect to one another. The external surface of the socket portion includes at least one vertical slot which is provided so that the semi-spherical head, which has a major diameter which is larger than the opening in the bottom of the element may be received within the open volume therein. The at least one slot resiliently expands to receive the head and contracts into position once the head is fully inserted, therein inhibiting the head from being retracted.

The exterior of the lower portion of the coupling element, into which the head is inserted, tapers outward slightly toward the bottom of the element, therein having a slightly wider bottom diameter than at the top of the lower portion. A locking ring, having a diameter equal to or greater than the top of the lower portion, but less than the diameter of the bottom of the lower portion, is disposed initially about the top of the lower portion.

Subsequent to proper positioning of the blade portion of the hook under the corresponding lamina, the coupling of the rod to the coupling element (as set forth in more detail hereinbelow), and the setting of the proper angulation of the coupling element relative to the hook, the locking ring may be forced by a sufficient application of pressure downward along the exterior of the lower portion of the coupling element. The locking ring therein applies an inward force against the walls of the interior chamber, and the corresponding narrowing of the vertical slots thereof. Once fully driven downward the locking ring causes the coupling element to be securely locked relative to the blade portion of the hook.

The intermediate portion of the coupling element comprises a recess in the side thereof, wherein the rod is retained. More particularly, at a position above the lower portion, a channel is formed in the side of the cylindrical body for receiving the rod. An external rod securing sleeve is also provided for holding the rod in the side recess and preventing it from moving relative thereto. The external rod securing sleeve is generally cylindrical in shape, having a hollow center for sliding over the top of the coupling element. The bottom of the sleeve includes two opposing downwardly extending members; forming therebetween a second channel. The sleeve, therefore, has a conformation which resembles an upside down U-shape and cups the rod from above. Subsequent to the placement of the rod in the channel, the rod securing sleeve is deposited on the coupling element such that the rod is positioned within the vertically aligned slots therein.

The locking ring on the lower portion is initially positioned so that the upper annular surface thereof extends vertically above the bottom ledge of the side recess of the intermediate portion, so that in its initial disposition in the channel, the rod seats on the locking ring. As the rod securing sleeve descends onto the coupling element to cup the rod, the rod is driven downward, causing the locking ring to descend along the exterior of the lower section, crush locking the head of the hook to the interior chamber of the coupling element. This driving force is enhanced dramatically by the application of a top locking nut onto the coupling element, as described more fully hereinbelow.

The upper portion of the coupling element comprises a threading onto which a locking nut may be inserted. The bottom surface of the nut is designed to mate with the top of the rod securing element. Engagement of the nut with the upper portion of the coupling element, and driving of the nut downward onto the upper portion of the coupling element causes the rod securing sleeve to be driven downward. The downward movement of the rod securing sleeve, in turn, drives the rod downward within the recess on the locking ring. Ultimately the inward radial force applied to the lower portion of the coupling element causes the at least one slot therein to close and for the head of the hook to be locked therewith. The rod, too, is then securely locked between the top of the locking ring and the sleeve, and is thereby prevented from axial or rotational movement.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 3:
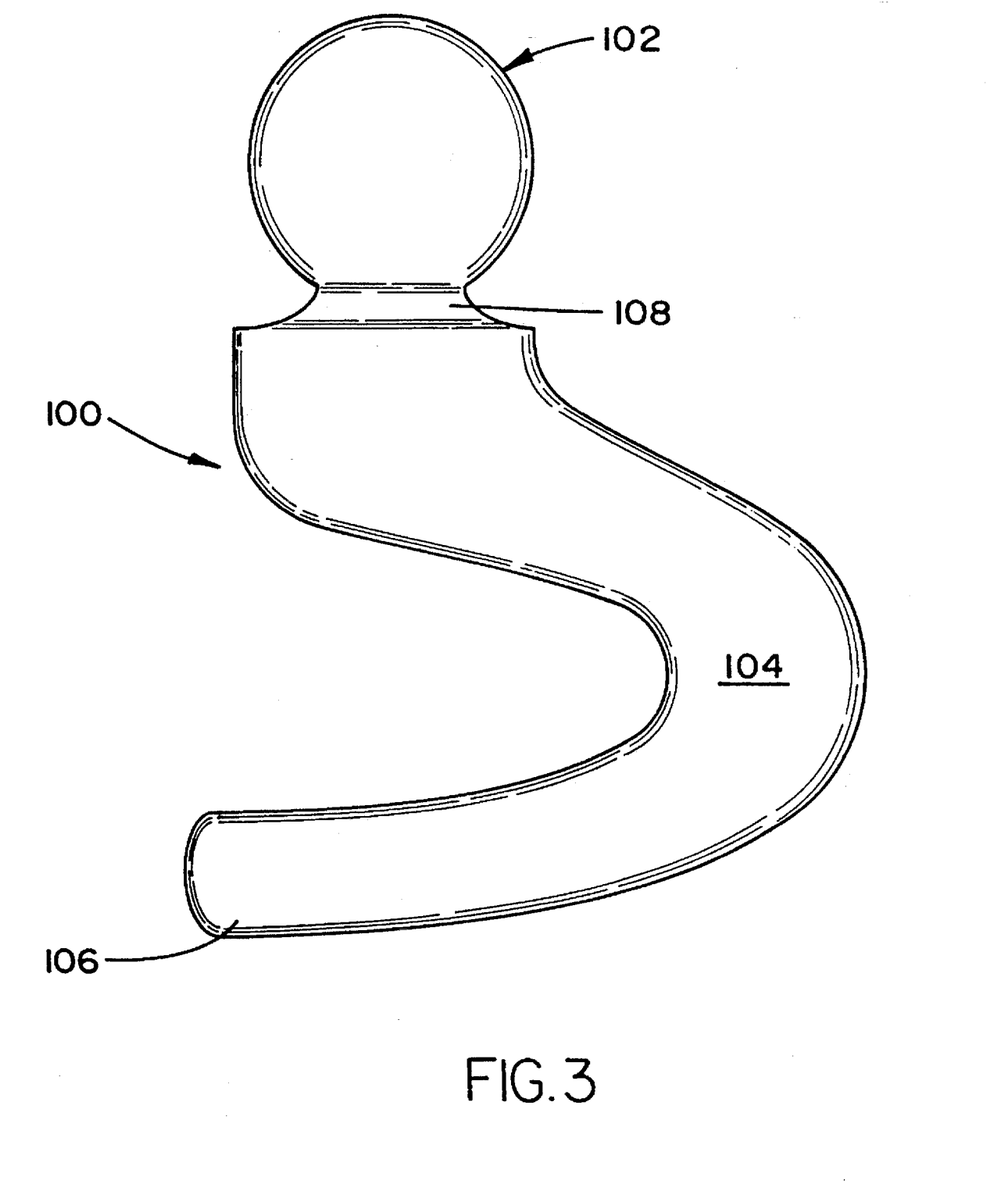
FIG. 3 is a side cross-sectional view of a blade portion of the hook of the present invention, said blade portion having a semi-spherical ball head.

Referring now to FIG. 3, a side view of the blade portion 100 of the hook device is provided. The blade portion 100 comprises a head portion 102 and a C-shaped portion 104. The lower extending branch 106 of the C-shaped portion 104 comprises a flat member which is understood to be the portion which is inserted under the lamina of the patient's spine. The semi-spherical head portion 102 is connected to upper extending branch of the C-shaped portion 104 at a neck portion 108.

The head portion 102 of the blade portion comprises a semi-spherical shape. It is understood that the semi-spherical shape is a section of a sphere. In the embodiment shown, the section is greater in extent than a hemisphere, and it correspondingly exhibits an external contour which is equidistant from a center point of the head. In a preferred embodiment, the major cross-section of the semi-spherical head 102 includes at least 270 degrees of a circle.

Figure 4:
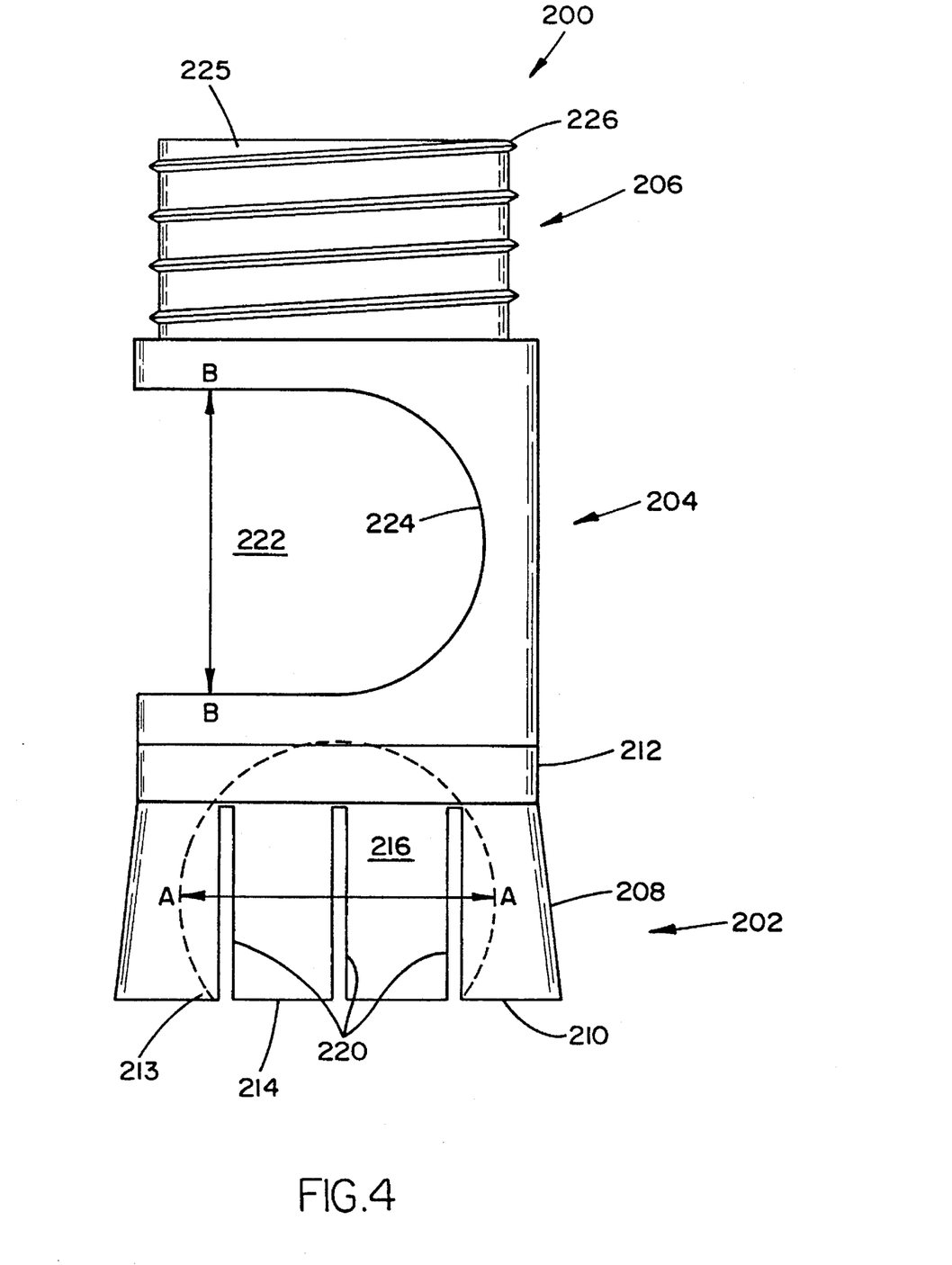
FIG. 4 is a side view of the side loading polyaxial coupling element of the present invention.

Referring now to FIG. 4, a first embodiment of the coupling element 200 of the present invention is shown in a side view, wherein critical features of the interior of the element are shown in phantom. The coupling element 200 comprises a generally cylindrical body which may be conceptually separated into a lower portion 202, an intermediate portion 204, and an upper portion 206, each of which shall be described more fully hereinbelow.

First, with respect to the lower portion 202, the exterior surface 208 of the body is tapered in the elongate direction such that the body is wider at the bottom 210 of the lower portion 202 than at the top 212 thereof. The bottom 210 of the element includes an expandable and contractable opening 214, defined by annular lip 213, which forms the mouth of an expandable and contractable interior chamber 216. The diameter of the opening 214, when otherwise unaffected by external deflecting forces, is more narrow than the maximum diameter A-A of the interior chamber 216. The interior chamber 216 has a generally curvate inner surface 218 which is correspondingly shaped to receive the semispherical head 102 of the blade portion 100.

The exterior surface of the lower portion 202 includes a series of slots 220 which extend vertically upward from the bottom 210 of the element to a point which is closer to the top 212 of the lower portion 202 than the maximum horizontal diameter A—A of the interior chamber. The slots 220 are provided in order that the application of an external deflecting force may widen or narrow the opening 214 therein permitting the insertion of an object, such as the head 102 of the blade portion, which is larger than the undeflected diameter of the opening 214, or conversely, providing for the retention of an object such as the same.

The intermediate portion 204 of the generally cylindrical body of the coupling element 200 includes a large removed section which forms a horizontal channel 222 in the side of the coupling element 200. The rod receiving channel 222 comprises a curvate inner wall 224. The horizontal depth of the inner wall 224 is established such that a circular support rod (see FIG. 8) which is positioned in the rod receiving channel 222 may nest fully within the coupling element 200, and does not extend beyond the lateral extent of the element, which would prevent a rod securing sleeve (such as shall be described with reference to FIG. 7) from sliding over the intermediate portion 204 of the element 200 to retain the rod within the channel 222. In the embodiment shown in FIG. 4, the vertical distance between the interior opposing surfaces of the channel (the distance being represented in FIG. 4 by line B—B) is greater than the anticipated diameter of the support rod to be positioned therein, such that the rod may be translated vertically within the channel 222 (the purpose for which is set forth herein below with respect to FIGS. 6–8).

The upper portion 206 of the coupling element 200 comprises a slightly narrower cylindrical core 225, having a threading 226 thereon. The upper portion 206, and the threading 226 thereon, is ideally suited for receiving a top locking nut (see FIG. 6).

Figure 5:
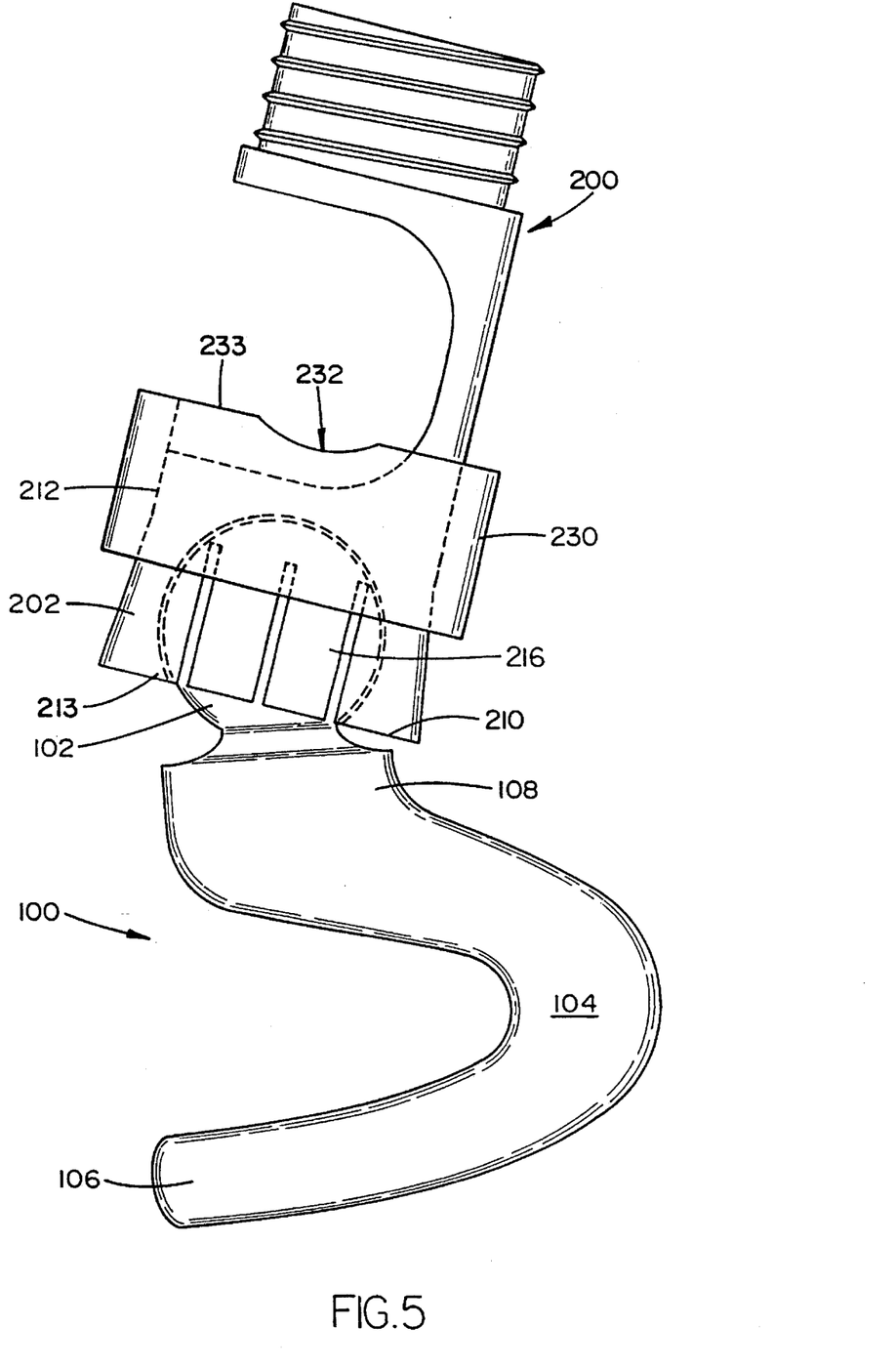
FIG. 5 is a side view of the coupling element of FIG. 4 shown mounted to the semi-spherical ball head of the blade portion as shown in FIG. 3, said coupling element having a locking ring disposed around the lower portion thereof.

Referring now to FIG. 5, the coupling element 200, as described more fully with respect to FIG. 4, is shown in a side view, wherein the head 102 of the blade portion 100 has been received within the interior chamber 216, and a locking ring 230 is shown in its pre-locked position about the top 212 of the lower portion 202. The head 102 is rotationally free to move relative to the coupling element 200, however, they are prevented from fully separating by the annular lip 213 at the bottom 210 of the lower portion 202. The locking ring 230 comprises a contiguous annular element having an inner diameter which is equal to the outer diameter of the lower portion 202 at the top 212 thereof. In order to lock the coupling element 200 relative to the blade portion 100, therein eliminating the freedom of the coupling element 200 to freely rotate or angulate on the ball head 102, the locking ring 230 must be forced downward relative to the coupling element 200.

It shall be understood that a dowel, protuberance, or other suitable means may be provided at or above the top 212 of the lower portion 202 so that the ring 230 may not be easily moved upward, and thereby preventing separation of the locking ring during handling prior to use. In addition, it shall be further understood that in its properly inserted orientation, it is desirable for coupling element 200 to be rotated approxiamtely 90 degrees relative to the blade portion 100 such that the channel 222 may receive therein a rod which is aligned substantially co-linearly with the lower branching portion 106 of the blade portion 100.

As shown in FIG. 5, the locking ring includes notches 232 on the top annular surface 233 thereof for superior seating of the rod thereon.

Figure 6:
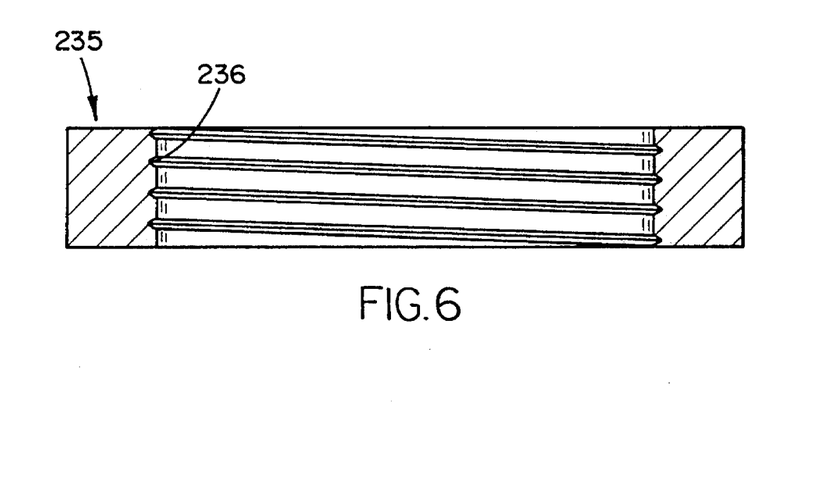
FIG. 6 is a top locking nut of the present invention.
Figure 7:
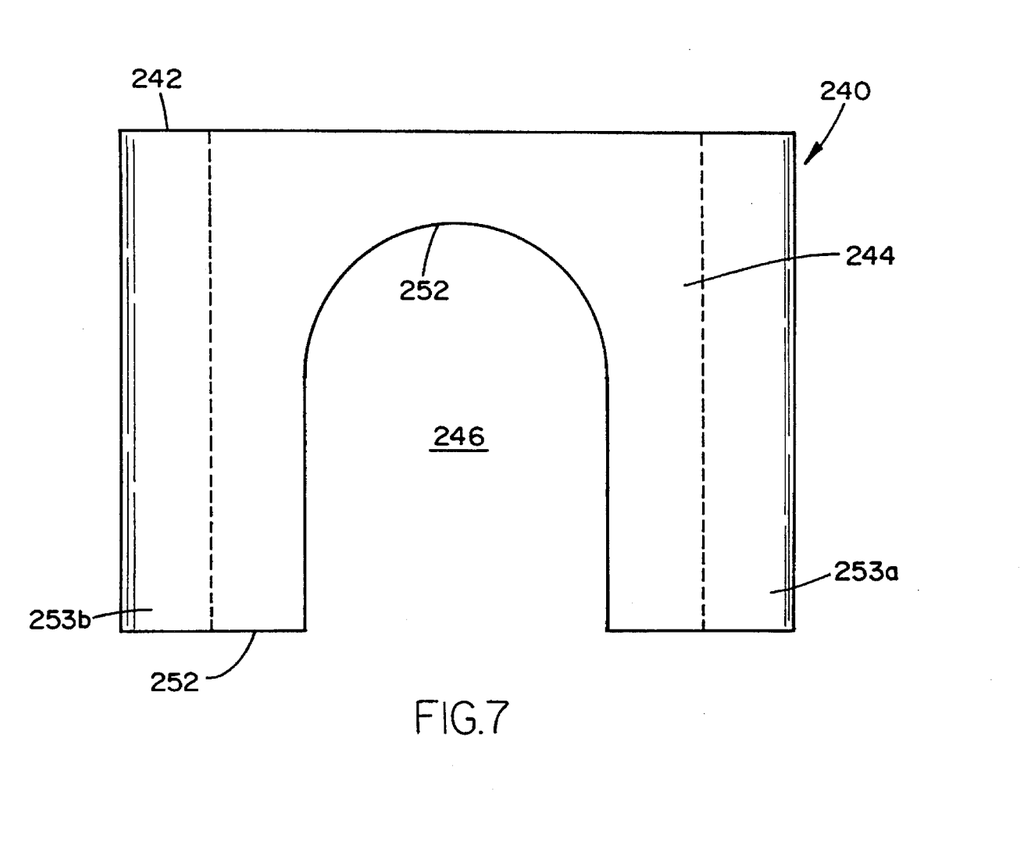
FIG. 7 is a rod retaining sleeve of the present invention.

Referring now to FIGS. 6 and 7, a top locking nut 235 and the rod securing sleeve 240 of the first embodiment are shown in side cross-section views. Referring specifically to FIG. 7, the rod securing sleeve 240 comprises a hollow cylindrical body 244 having a flat annular top surface 242 and a curved bottom surface 252. In fact, the bottom surface 252 is so curved as to have an upside-down U-shape defined by a pair of downwardly extending members 253a, 253b formed of the cylindrical body 244. These downwardly extending members 253a, 253b, in turn, define diametrically opposing vertical slots 246, which together provide a passage through the bottom of the sleeve for cupping a rod placed therethrough. The interior diameter of the sleeve 240 is equal to the outer diameter of the intermediate portion 204 of the coupling element 200, so that it may be placed over the top portion 206 of the coupling element.

Referring now to FIG. 6, the nut 235 comprises an inner threading 236 which is intended to mate with the threading 226 on the upper portion 206 of the coupling element 200.

The bottom surface 238 of the nut 235 is intended to seat against the top surface 242 of the rod securing sleeve 240, but is permitted to rotate relative to the sleeve, therein providing a means for driving the sleeve 240 downward (as more fully described hereinbelow with respect to the full assembly of the device, and with respect to FIG. 8).

Figure 8:
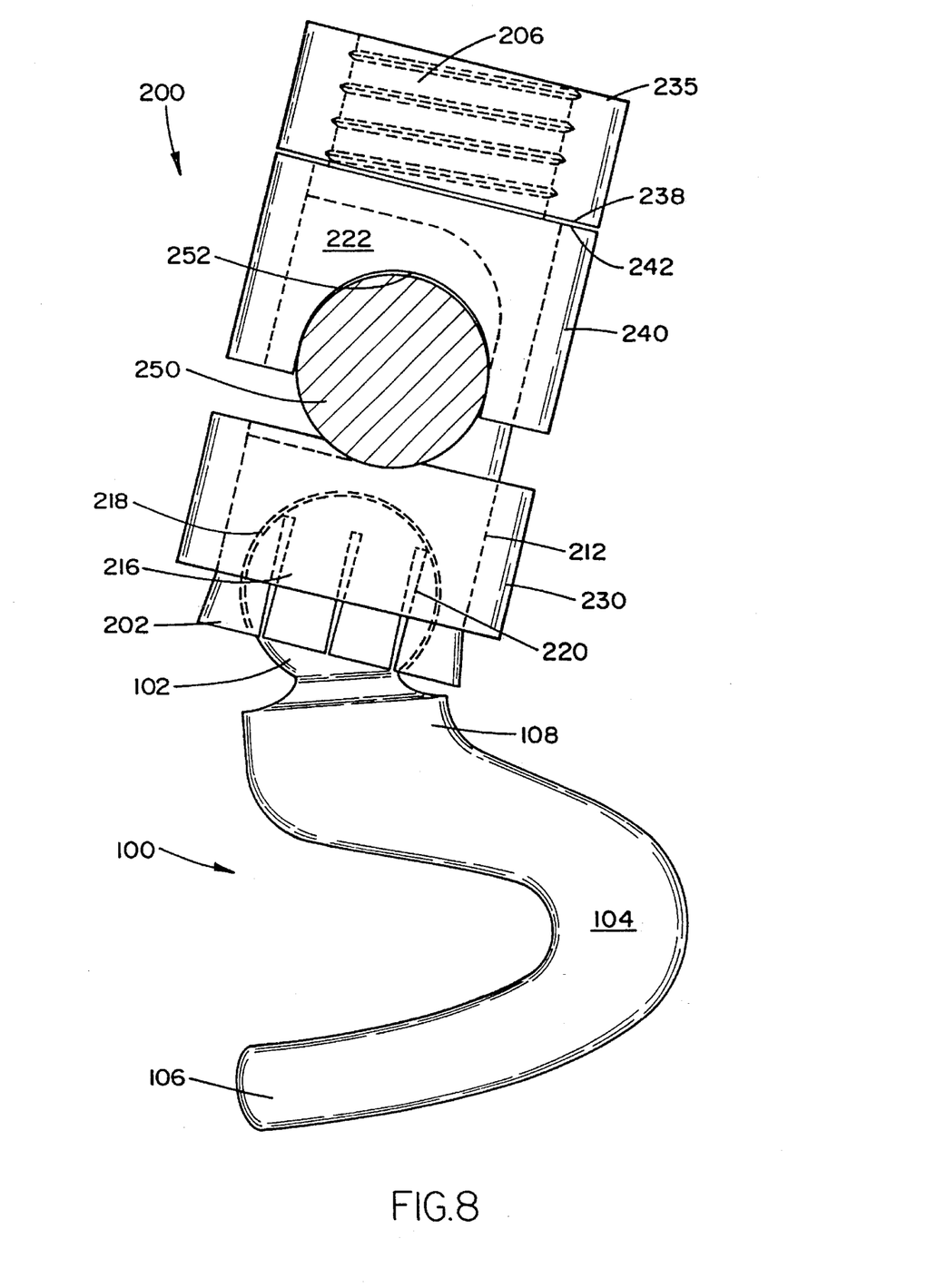
FIG. 8 is a fully assembled hook of the present invention shown with a support rod secured therein.

With reference now to FIG. 8, which shows a side view of the fully locked coupling element, rod, and hook system, the preferred method of implantation and assembly is described hereinbelow. (It shall be understood that, as with FIG. 5, the desired disposition of the coupling element 200, relative to the blade portion 100 is rotated approximately 90 degrees from the view provided in FIG. 8. More particularly, the coupling element 200, when properly implanted, is oriented relative to the blade portion such that the rod portion 250 extends substantially co-linearly with the direction of the blade portion.) First, the blade portion 100 is positioned on the lamina (not shown) such that the lower extending branch portion 106 thereof is positioned under the lamina and in the spinal canal. It is critical that the lower extending branch portion 106 be positioned as close to flush against the lamina as possible.

The head 102 of the blade portion 100 is then inserted into the interior chamber 216 of the coupling element 200. (This step may, of course, be taken prior to the positioning of the blade portion relative to the lamina.) At this point in the assembly process, the locking ring 230 has not yet been forced downward along the outwardly tapered lower portion 202 (as shown in FIG. 5) thereby providing the coupling element 200 with the capacity to rotate and angulate relative to the positioned blade portion 100 one another. This permits the support rod 250 may be properly nested within the rod receiving channel 222. After the rod 250 is appropriately positioned, the rod securing sleeve 240 is dropped over the element, such that the rod extends outward through the diametrically opposed vertical slots 246 in the sleeve 240.

At this stage of the assembly, the head 102 and the coupling element 200 remain polyaxially disposed relative to one another, thereby being rotationally free, and the locking ring 230 remains positioned at the top 212 of the lower portion 202 of the element. The rod securing sleeve 240 is prevented from fully descending onto the coupling element 200 by the top surface of the support rod 250, the bottom surface thereof being initially prevented from translating downward by the locking ring 230.

Once the proper angulation of the coupling element to the blade portion 100, and the secure nesting of the rod 250 within the receiving channel 222, have been established, the top locking nut 235 is threaded onto the upper portion 206 of the coupling element 200. The lower surface 238 of the nut 235 seats against the top surface 242 of the rod securing sleeve 240. As the nut 235 rotates, and descends relative to the coupling element, the rod securing sleeve 240 is driven downward. This motion forces the support rod 250 to translate downward in the channel 222, causing the locking ring 230 to translate downward along the lower portion 202 of the coupling element 200. By descending along the tapered lower portion 202 of the element, the locking ring 230 provides an inwardly directed deflecting force which causes the slots 220 in the lower portion 202 of the element to narrow so that the ring may proceed downward. This deflection inward causes the inner surface 218 of the interior chamber 216 to crush lock against the head 102 of the blade portion 100. This clamping force locks the angulation of the coupling element 200 relative to the blade portion 100. Ultimately, once the locking ring 230 cannot be translated down any further, the downward force of the nut 235 against the rod securing sleeve 240 causes the bottom cupping surface 252 of the sleeve 240 to lock the rod 250 between itself and the top surface of the locking ring 230. This locking prevents the rod 250 from sliding relative to the assembled structure (along an axis which is perpendicular to the plane of FIG. 8). The full insertion of the top locking nut 235, therefore, locks the rod 250 to the coupling element 200, as well as the blade portion 100 to the coupling element 200.

While there has been described and illustrated a single embodiment of a lamina hook having a polyaxial coupling element body, it will be apparent to those skilled in the art that variations and modifications are possible without deviating from the broad spirit and principle of the present invention. The present invention shall, therefore, be limited solely by the scope of the claims appended hereto.

We claim:

1. A polyaxial hook assembly for use with orthopedic rod implantation apparatus, comprising:
   a blade portion, having a curved shape for cupping the lamina, a lower extending member for disposition beneath the lamina, and a semi-spherical head which is disposed above the lower extending member;
   a coupling element including
      an expandable and contractable interior chamber for receiving therein said semi-spherical head, said interior chamber further having an expandable and contractable opening for receiving therethrough said semi-spherical head,
      a rod receiving channel formed in a side thereof for receiving therein a support rod of said orthopedic rod implantation apparatus, and
      a surface threading disposed on an upper exterior portion thereof;
   a locking ring mounted around said coupling element, the downward translation of said ring providing a force which causes said interior chamber and said opening thereof to contract, therein locking the blade portion to the coupling element;
   a rod securing sleeve, positionable around, and in rod securing relationship with, said rod receiving channel for securing said rod therein;
   a top locking nut, mateable with said surface threading.

2. The coupling assembly as set forth in claim 1, wherein said coupling element further comprises at least one vertical slot extending upward from said opening, therein rendering said interior chamber and said opening expandable and contractable.

3. The coupling assembly as set forth in claim 2, wherein a portion of said coupling element which contains said interior chamber comprises an exterior surface taper, said portion being wider at said opening, whereby the downward translation of said locking ring causes the interior chamber and said opening to contract.

4. The coupling assembly as set forth in claim 3, wherein a bottom surface of said top locking nut seats against a top surface of said rod securing sleeve, and the support rod seats against a top surface of said locking ring, the downward translation of said top locking nut thereby causing said support rod to be crush locked between said rod securing sleeve and said locking ring.

5. The coupling assembly as set forth in claim 4, wherein said downward translation of said nut on said exterior threading of said coupling element causes the downward translation of said locking ring to crush lock the semi-spherical head within said interior chamber.

6. A polyaxial screw and coupling element assembly for use with orthopedic rod implantation apparatus, comprising:

a blade portion, having a curved shape for cupping the lamina, a lower extending member for disposition beneath the lamina, and a semi-spherical head which is disposed above the lower extending member;

a coupling element having lower, intermediate, and upper portions thereof, said lower portion including a taper wherein the bottom of the portion is wider than the top, said coupling element including at least one vertical slot formed in said lower portion extending upward from a bottom of said lower portion, an opening in said bottom of said lower portion, for receiving therethrough said semi-spherical head, said opening being expandable and contractable by forces applied to said at least one vertical slot;

an interior chamber disposed within said lower portion, for receiving therein said semi-spherical head, a rod receiving channel formed in the side of said intermediate portion for receiving therein a support rod of said orthopedic rod implantation apparatus, and an exterior threading disposed on an exterior of said upper portion;

a locking ring mounted around said lower portion, the downward translation of said ring applying an inward force to said at least one vertical slot and therein locking the semi-spherical within the coupling element;

a rod securing sleeve comprising a hollow cylindrical body, having opposing vertical slots, said sleeve being positionable around said intermediate portion for securing said rod within said intermediate portion, wherein said rod passes through said vertical slots of said sleeve; and a top locking nut which is mateable with said exterior threading.

7. The coupling assembly as set forth in claim 6, in combination with a support rod, wherein a bottom surface of said top locking nut seats against a top surface of said rod securing sleeve, the support rod seats on a top surface of the locking ring, and the downward translation of said top locking nut causes said support rod to be locked between a bottom surface of the rod securing sleeve and the top surface of the locking ring.

8. The coupling assembly a rod as set forth in claim 7, wherein the downward translation of said nut on said exterior threading of said coupling element causes the downward translation of the support rod within the channel, and causes the locking ring to descend and crush lock the semi-spherical head within said interior chamber.

9. An orthopedic rod implantation apparatus, comprising:

at least one elongate rod;

a plurality of polyaxial hook assemblies for coupling said elongate rod to lamina of a spine, each of said hook assemblies including a blade portion, having a curved shape for cupping the lamina, a lower extending member for disposition beneath the lamina, and a semi-spherical head which is disposed above the lower extending member;

a coupling element having, an expandable and contractable interior chamber for receiving therein said curvate head, said interior chamber having an expandable and contractable opening for receiving therethrough said semi-spherical head, a rod receiving channel in a side thereof for receiving therein a rod of said orthopedic rod implantation apparatus, and a surface threading disposed on an upper exterior portion thereof;

a locking ring mounted around said coupling element, the downward translation of said ring providing a force which causes said interior chamber and said opening thereof to contract, therein locking the blade portion to the coupling element;

a rod securing sleeve, positionable around, and in rod securing relationship with, said rod receiving channel for securing said rod therein;

a top locking nut, mateable with said surface threading.

10. The apparatus as set forth in claim 9, wherein each of said coupling elements further comprises at least one vertical slot extending upward from said opening, therein rendering said interior chamber and said opening expandable and contractable.

11. The apparatus as set forth in claim 10, wherein a portion of said coupling element which contains said interior chamber comprises an exterior surface taper, said portion being wider at said opening, whereby the downward translation of said locking ring causes the interior chamber and said opening to contract.

12. The apparatus as set forth in claim 11, wherein a bottom surface of said top locking nut seats against a top surface of said rod securing sleeve, the support rod seats against a top surface of said locking ring, whereby the downward translation of said top locking nut causes said support rod to be locked between a bottom surface of said rod securing sleeve and said top surface of said locking ring.

13. The apparatus as set forth in claim 12, wherein the downward translation of said nut on said exterior threading of said coupling element causes the downward translation of said support rod with said channel, which causes the downward translation of the locking ring so as to crush lock the semi-spherical head within said interior chamber.

* * * * *